United States Patent [19]

Warner et al.

[11] Patent Number: 5,169,429
[45] Date of Patent: Dec. 8, 1992

US005169429A

[54] HYBRIDIZATION OF SUNFLOWERS AND SAFFLOWERS

[75] Inventors: Harlow L. Warner, Hatboro, Pa.; Gerard Sutra, Toulouse, France

[73] Assignee: Monsanto Company, St. Louis, Mo.

[21] Appl. No.: 726,074

[22] Filed: Jul. 5, 1991

Related U.S. Application Data

[63] Continuation of Ser. No. 421,481, Oct. 13, 1989, abandoned.

[30] Foreign Application Priority Data

Oct. 14, 1988 [GB] United Kingdom ............... 8824143

[51] Int. Cl.$^5$ .............................................. A01N 43/58
[52] U.S. Cl. ........................................... 71/92; 71/65
[58] Field of Search ........................................ 71/92, 65

[56] References Cited

U.S. PATENT DOCUMENTS 4,345,934 8/1982 Fujimoto .................................. 71/92
4,623,378 11/1986 Dürr et al. ............................... 71/92

FOREIGN PATENT DOCUMENTS 37133 10/1981 European Pat. Off. .
1596611 8/1981 United Kingdom .

Primary Examiner—Richard L. Raymond
Assistant Examiner—Brian G. Bembenick
Attorney, Agent, or Firm—Howard C. Stanley; Grace L. Bonner

[57] ABSTRACT

A method of inducing male sterility in a dicotyledonous plant which comprises treating the plant prior to, during or post meiosis with an amount of a substituted 4-oxo-1-phenyl-1,4-dihydropyridazine, which is effective to produce male sterility in the plant.

5 Claims, No Drawings

HYBRIDIZATION OF SUNFLOWERS AND SAFFLOWERS

This is a continuation of application Ser. No. 07/421,481, filed Oct. 13, 1989 (abandoned).

The present invention relates to the use of compounds as chemical hybridisation agents on dicotyledonous plants, in particular by inducing selective male sterility. The compounds of the invention are disclosed in GB 1596611-A along with the method of preparation and utility as chemical hybridisation agents on cereal grain plants and as plant growth regulators. The applicants have now discovered that the compounds of the invention are effective chemical hybridisation agents in dicotyledonous plants.

GB 2145411 discloses certain gametocidal pyridazinylcarboxylic acid derivatives useful for influencing generative plant growth and for producing male sterile plants. EP-A-0037133 discloses certain gametocidal pyridazinone compounds useful for sterilizing the male anthers of plants including small grain cereal plants and using them as a method of producing F1 hybrid seed. EP-A-0138662 discloses certain 3-carboxyalkyoxyaminocarbonylpyridazines useful as pollen suppressants for cereal grain plants and their use for producing hybrid seed. EP-A-0138663 discloses certain pyridazolyamines as pollen suppressants for cereal grain plants and their use for producing hybrid seed.

Dicotyledonous plants provide an important source of food for humans and animals and raw materials for industry. In particular crops such as soybean, sunflower, oilseed rape, sugarbeet, cotton, potato and various other staple vegetables.

Dicotyledonous plants differ from cereal crops which are monocotyledonous plants in many physiological aspects which are well known to the plant scientist. Previous disclosures have described effective chemical hybridisation activity in monocotyledonous plants, however, this activity has not been previously shown in dicotyledonous species for the compounds of the present invention.

GB 1596611-A discloses hybridisation effects on cereal grain crops and other plant growth regulator effects in non-cereal species. Hybridisation is achieved through inducement of male sterility where this term includes both actual male sterility, as evidenced by a lack of male flower parts or by sterile pollen, and functional male sterility, in which the male flower parts are unable to cause pollination. Other plant growth regulator effects are likely to be a consequence of the action of the compounds on plant growth hormones. This invention is concerned only with chemical hybridisation of dicotyledonous species and inducement of male sterility therein.

According to the present invention there is provided a method of inducing male sterility in an agricultural or horticultural dicotyledonous plant which comprises treating the plant prior to, during or post meiosis with an amount, which is effective to produce male sterility in the plant, of the compound of formula (I)

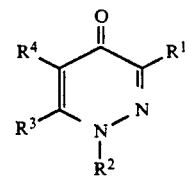

wherein $R^1$ is a carboxy group (—COOH), or an agronomically acceptable salt thereof, or alkoxycarbonyl preferably having up to 12 carbon atoms in the alkoxy moiety, most preferably from 1 to 4 carbon atoms in the alkoxy moiety;

$R^2$ is phenyl or substituted phenyl having up to three substituents collectively having a total of 0 to 6 carbon atoms, the substituents being selected from alkyl, $C_4H_4=$ forming a naphthyl group, alkoxy, phenoxy, halogen, nitro, perhaloalkyl, alkyoxyalkyl, alkoxyalkoxy, amino, alkyl- or dialkylamino, cyano, alkoxycarbonyl, carbamoyl, alkyl- or dialkylcarbamoyl, sulpho, sulphonamide, alkylcarbonyl, carboxyalkyl, alkanoyloxy, haloalkyl, alkanoylamino, alkylthio, alkylsulphinyl and alkylsulphonyl;

$R^3$ is alkyl, preferably having from 1 to 4 carbon atoms; and $R^4$ is hydrogen, alkyl, preferably having from 1 to 4 carbon atoms, or halogen, preferably a bromine or a chlorine atom.

In a preferred embodiment of the invention, $R^1$ is a carboxy group of a salt thereof, $R^3$ is a methyl group, $R^4$ is a hydrogen atom, a halogen atom, or a propyl group and $R^2$ is a substituted phenyl group.

When $R^1$ is a salt of a carboxy group, an alkali metal, alkaline earth metal, or a transition metal can provide the cation. The cation can also be an ammonium or substituted ammonium group. Representative metal salt cations include alkali metal cations, which are preferred, such as sodium, potassium and lithium; alkaline earth metal cations, such as calcium, magnesium, barium and strontium, or heavy metal cations, such as zinc, manganese, cupric, cuprous, ferric, ferrous, titanium and aluminium. Among the ammonium salts are those in which the ammonium cation has the formula $NZ^1Z^2Z^3Z^4$, wherein $Z^1$, $Z^2$, $Z^3$ and $Z^4$ (which may be the same or different) represent hydrogen, hydroxy, $(C_1-C_4)$ alkoxy, $(C_1-C_{20})$ alkyl, $(C_3-C_8)$ alkenyl, $(C_3-C_8)$ alkynyl, $(C_2-C_8)$ hydroxyalkyl, alkoxyalkyl having from 2 to 8 carbon atoms, $(C_2-C_6)$ aminoalkyl, $(C_2-C_6)$ haloalkyl, substituted or unsubstituted phenyl, substituted or unsubstituted phenylalkyl having up to 4 carbon atoms in the alkyl moiety, amino or alkyl-substituted amino.

Alternatively, any two of $Z^1$, $Z^2$, $Z^3$, or $Z^4$ can be joined together to form, with the nitrogen atom, a 5- or 6-membered heterocyclic ring which optionally has up to one additional hetero oxygen, nitrogen, or sulphur atom in the ring and which is preferably saturated as in a piperidine, morpholine, pyrrolidine, or piperazine ring. Another alternative is that any three of $Z^1$, $Z^2$, $Z^3$, or $Z^4$ can be joined together to form, with the nitrogen atom, a 5- or 6-membered aromatic heterocyclic ring, such as a pyrrole or pyridine ring. When the ammonium group contains a substituted alkyl, substituted phenyl, or substituted phenylalkyl group the substituents will generally be selected from halogen, $(C_1-C_8)$ alkyl, ($C_1$–$C_4$) alkoxy, hydroxy, nitro, trifluoromethyl, cyano, amino and ($C_1$–$C_4$) alkylthio. Such substituted phenyl groups preferably have up to two such substituents. Representative ammonium cations include ammonium, dimethylammonium, 2-ethylhexylammonium, bis (2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hyxylammonium, triethylammonium, trimethylammonium, tri(n-butyl)ammonium, methoxyethyl-ammonium, diisopropylammonium, pyridinium, diallylammonium, pryazolium, propargylammonium, dimethylhydrazinium, hydroxyammonium, methoxyammonium, dodecylammonium, octa-decylammonium, 4-dichlorophenylammonium, 4-nitrobenzylammonium, benzyltrimethylammonium, 2-hydroxyethyldimethyl-octadecylammonium, 2-hydroxyethyldiethyloctylammonium, decyltrimethylammonium, hexyltriethylammonium, and 4-methyl-benzyltrimethylammonium.

Representative embodiments of $R^2$ include a phenyl group substituted with alkyl having up to 4 carbon atoms; alkoxy having up to 4 carbon atoms; fluorine, chlorine, bromine or iodine; trifluoromethyl, alkoxyalkyl having up to 6 carbon atoms; alkoxyalkoxy having up to 6 carbon atoms; alkyl- or dialkylamino groups having not more than 4 carbon atoms in each alkyl substituent; alkoxycarbonyl having up to 4 carbon atoms in the alkoxy moiety; alkyl or dialkylcarbamoyl groups having not more than 4 carbon atoms in each alkyl substituent; alkoxycarbonyl or carboxyalkyl each having up to 4 carbon atoms in the alkyl moiety; alkanoyloxy having up to 4 carbon atoms; alkanoylamino having up to 4 carbon atoms; alkylthio having up to 4 carbon atoms; alkylsulphinyl having up to 4 carbon atoms; and alkylsulphonyl having up to 4 carbon atoms. The most preferred substitutents on the phenyl group are 1 or 2 halogen atoms, a ($C_1$–$C_4$) alkyl, preferably a methyl group, a ($C_1$–$C_4$) alkoxy, preferably a methoxy group, or a tri-fluoromethyl group, and salts and esters of the above acids.

Typical compounds within the scope of this invention include:

1-phenyl-1,4-dihydro-4-oxo-6-methylpyridazine-3-carboxylic acid,
1-(4-chlorophenyl)-1,4-dihydro-4-oxo-6-methylpyridazine-3-carboxylic acid,
1-(4-fluorophenyl)-1,4-dihydro-4-oxo-6-methylpyridazine-3-carboxylic acid
1-(4-btomophenyl)-1,4-dihydro-4-oxo-6-methylpyridazine-3-carboxylic acid,
1-(4-bromophenyl)-1,4-dihydro-4-oxo-6-methylpyridazine-3-carboxylic acid,
1-(4-iodophenyl)-1,4-dihydro-4-oxo-6-methylpyridazine-3-carboxylic acid,
1-(3-fluorophenyl)-1,4-dihydro-4-oxo-6-methylpyridazine-3-carboxylic acid,
1-(3-chlorophenyl)-1,4-dihydro-4-oxo-6-methylpyridazine-3-carboxylic acid,
1-(3-bromophenyl)-1,4-dihydro-4-oxo-6-methylpyridazine-3-carboxylic acid,
1-(3,4-dichlorophenyl)-1,4-dihydro-4-oxo-6-methylpyridazine-3-carboxylic acid,
1-(2-fluorophenyl)-1,4-dihydro-4-oxo-6-methylpyridazine-3-carboxylic acid,
1-(2-chlorophenyl)-1,4-dihydro-4-oxo-6-methylpyridazine-3-carboxylic acid,
1-(4-trifluoromethylphenyl)-1,4-dihydro-4-oxo-6-methylpyridazine-3-carboxylic acid,
1-(3-trifluoromethylphenyl)-1,4-dihydro-4-oxo-6-methylpyridazine-3-carboxylic acid,
1-phenyl-1,4-dihydro-4-oxo-6-ethylpyridazine-3-carboxylic acid,
1-(4-chlorophenyl)-1,4-dihydro-4-oxo-6-ethylpyridazine-3-carboxylic acid,
1-(4-fluorophenyl)-1,4-dihydro-4-oxo-6-ethylpyridazine-3-carboxylic acid,
1-(3,4-dichlorophenyl)-1,4-dihydro-4-oxo-6-ethylpyridazine-3-carboxylic acid,
1-phenyl-1,4-dihydro-4-oxo-6-propylpyridazine-3-carboxylic acid,
1-phenyl-1,4-dihydro-4-oxo-5,6-dimethylpyridazine-3-carboxylic acid,
1-(4-chlorophenyl)-1,4-dihydro-4-oxo-5,6-dimethylpyridazine-3-carboxylic acid,
1-phenyl-1,4-dihydro-4-oxo-5-ethyl-6-methylpyridazine-3-carboxylic acid,
1-phenyl-1,4-dihydro-4-oxo-5,6-diethylpyridazine-3-carboxylic acid,
1-(4-methylphenyl)-1,4-dihydro-4-oxo-6-methylpyridazin 3-carboxylic acid,
1-(2-chloro-4-methylphenyl)-1,4-dihydro-4-oxo-6-methylpyridazine-3-carboxylic acid,
1-(2,4,6-trichlorophenyl)-1,4-dihydro-4-oxo-6-methylpyridazine-3-carboxylic acid,
1-(3-ethoxyphenyl)-1,4-dihydro-4-oxo-6-methylpyridazin 3-carboxylic acid,
1-(4-methylthiophenyl)-1,4-dihydro-4-oxo-6-methyl pyridazine-3-carboxylic acid,
1-(3-cyanophenyl)-5-bromo-1,4-dihydro-4-oxo-6-ethyl pyridazine-3-carboxylic acid,
1-phenyl-5-bromo-1,4-dihydro-4-oxo-6-methylpyridazine-3-carboxylic acid,
1-(3-chlorophenyl)-5-chloro-1,4-dihydro-4-oxo-6-methylpyridazine-3-carboxylic acid,
1-(4-chlorophenyl)-5-bromo-1,4-dihydro-4-oxo-6-ethyl pyridazine-3-carboxylic acid, and salts and esters of the above acids.

The compounds of formula (I) can be prepared by the methods outlined in GB 1596611-A or known methods for analogous compounds. The physical properties of the compounds in question can be found in Table 1 of GB 1596611-A.

The compounds of formula (I) are particularly useful as chemical hybridisation agents in dicotyledonous crops, such as sunflower, safflower, sugar beet, soybean, rape and cotton. As chemical hybridisation agents, the compounds effectively induce a high degree of selective male sterility, without also inducing significant female sterility, in the treated plants and without causing significant growth inhibition of the treated plants. As used herein, the term male sterility includes both actual male sterility, as evidenced by a lack of male flower parts or by sterile pollen, and functional male sterility, in which the make flower parts are unable to cause pollination.

The compounds are applied in any amount which will be sufficient to effect the desired plant response without causing any undesirable or phytotoxic response. The compounds are generally applied to the crops to be treated at a rate of 0.035 to 22 kg per hectare and preferably 0.1 to 12 kg per hectare.

The rate of application will vary depending on the crop being treated, the compound being used for treatment and factors related to the environment.

To obtain hybrid seed, the following procedure is generally employed. The two parents to be crossed are planted in alternate strips. The female parent is treated with a compound of formula (I). The male sterile parent thus produced will be pollinated by pollen from male-fertile parent, and the seed produced by the male-sterile parent will be hybrid seed which can then be harvested by conventional means.

The compound of formula (I) can be applied to the plant by foliar application. This method is most effective for inducing male sterility when the compound is applied between flower initiation and meiosis or post meiosis. The compounds of formula (I) can also be applied by soaking the seed in a liquid formulation containing the active compound or by coating the seed with the compound.

In seed treatment applications, the compounds of formula (I) will generally be applied at a rate of about 0.25 to 10 kg per hundred kg of seed. The compounds may also be applied to the soil as granules with corresponding root-uptake of active ingredient.

The compounds of formula (I) can be used as hybridisation agents together, for example, in admixtures with other plant growth regulators such as auxins (e.g., indoleacetic acid, indolebutyric acid, naphthoxyacetic acid or naphthylacetic acid), quinchlorac, quinmerac, gibberellins (e.g., $GA_3$, $GA_4$, or $GA_7$), ethylene-releasing agents such as ethephon, pyridones, cytokinins (e.g., kinetin, diphenylurea, benzimidazole, benzyladenine or benzylaminopurine), maleic hydrazide, succininc acid, phenoxyacetic acids (e.g., 2,4-D or MCPA), 2,2-dimethylhydrazide, choline and its salts, (2-chloro-ethyl)-trimethylammonium chloride, substituted benzoic acids (e.g., triiodobenzoic acid), tributyl-2,4-dichlorobenzylphosphonium chloride, polymeric N-vinyl-2-oxazolidinones, tri(dimethylaminoethyl)phosphate and its salts, and N-dimethylamino-1,2,3,6-tetrahydrophthalamic acid and its salts, morphactins (e.g., chlorfluorecol), glyphosate, glyphosine, long chain fatty alcohol and acids, dikegulac, fluoridamid, mefluidide, mepiquat, carbetamide, methyl-3,6-dichloroanisate, daminozide, asulam, abscisic acid, isopyrimol, difenzoquat, benzoylpropethyl 3,6-dichloropicolinic acid, fenpentezol, uniconazole, triapenthanol, flurpirimidol, paclobutrazol, tetcyclacis, and tecnazene. Under some conditions the compounds of formula (I) may be used advantageously with agricultural pesticides such as herbicides, fungicides, insecticides and plant bactericides.

One or more of the compounds of formula (I) can be applied to the growth medium or to the plants to be treated either by itself or themselves in a gametocidal composition or, as is generally done, as a component in a growth regulant composition or formulation which also comprises an agronomically acceptable carrier such as, for example, a carrier or diluent which is agronomically acceptable but pharmaceutically unacceptable. By "agronomically acceptable carrier" is meant any substance which can be used to dissolve, disperse, or diffuse a compound in the composition without impairing the effectiveness of the compound and which by itself has no detrimental effect on the soil, equipment, crops, or agronomic environment. The growth regulant compositions can be either solid or liquid formulations or solutions. For example, the compounds can be formulated as wettable powders, emulsifiable concentrates, dusts granular formulations, aerosols, or flowable suspension or emulsion concentrates. In such formulations, the compounds are extended with a liquid or solid carrier, and, when desired suitable surfactants are incorporated.

It is usually desirable, particularly in foliar applications, to include adjuvants, such as wetting agents, spreading agents, dispersing agents, stickers, adhesives, and the like, in accordance with agricultural practices.

The compounds of formula (I) can be dissolved in any appropriate solvent. Examples of solvents which are useful in the practice of this invention include water, alcohols, glycol ethers, esters, ketones, aromatic hydrocarbons, halogenated hydrocarbons, dimethylformamide, dioxane and dimethyl sulphoxide. Mixtures of these solvents can also be used. The concentration of the solution can vary from about 2% to about 98% by weight with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone or methyl oleate, or in mixtures of these solvents, together with an emulsifying agent or a surfactant which permits dispersion in water. Suitable emulsifiers include, for example, the ethylene oxide derivatives of alkylphenols or long-chain alcohols, mercaptans, carboxylic acids, and reactive amines and partially esterified polyhydric alcohols.

Solvent-soluble sulphates or sulphonates, such as the alkaline earth salts or amine salts of alkylbenzenesulphonates and the fatty alcohol sodium sulphates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilising agent such as a water soluble cellulose derivative or a water-soluble salt of a polyacrylic acid. The concentration of the active ingredient in emulsifiable concentrates is usually about 10% to 60%, or even as high as 75%, by weight. Aqueous suspension concentrates can be used by fine grinding of the active ingredient as a suspension in water, with the addition of dispersing agents and the like.

Wettable powders suitable for spraying, can be prepared by admixing the active compound with a finely divided solid, such as clays, in organic silicates and carbonates, and silicas and incorporating wetting agents sticking agents, and/or dispersing agents in such mixtures.

The concentration of active ingredients in such wettable powder is usually in the range of about 20% to 98% by weight, preferably about 40% to 75%. A dispersing agent may generally constitute about 0.5% to about 3% by weight of the wettable powder, and a wetting agent may generally constitute from about 0.1% to about 5% by weight of the composition.

Water disperable grains can be prepared by the same process as for wettable powders, followed by extrusion or agglomeration to produce free flowing grains which are non-dusty and redisperse into water. The resulting dispersion can be sprayed by normal means.

Dusts can be prepared by mixing the active compounds with finely divided inert solids which may be organic or inorganic in nature. Materials useful for this purpose include, for example, botanical flours, silicas, silicates, carbonates and clays.

One convenient method of preparing a dust is to dilute a wettable powder with a finely divided carrier.

Dust concentrates containing about 20% to 80% of the active ingredient are commonly made and are subsequently diluted to about 1% to 10% by weight use concentration.

Granular formulations can be prepared by impregnating a solid such as granular fuller's earth, vermiculite, attapulgite, gypsum, pumice, sand, limestone, ground corn cobs, seed hulls, including bran or other grain hulls or similar material. A solution of one or more of the compounds in a volatile organic solvent can be sprayed or mixed with the granular solid and the solvent then removed by evaporation. The granular material can have any suitable size, with a preferable size range of 16 to 60 mesh (U.S. Standard Sieve Series). The active compound will usually comprise about 2 to 15% by weight of the granular formulation. Granules can also be obtained by extruding or pelletting powdered combinations of active ingredient and mineral fillers or salts, using suitable binding agents such as water, polyglycols, lignosulphonates, polymers and resin solutions and the like and coating onto fertilizer prills and the like.

Salts of the compounds of the invention can be formulated and applied as aqueous solutions or oil emulsifiable concentrates. The salts will typically comprise about 0.05 to about 50% by weight, preferably about 0.1% to about 10%, of the solution. These compositions can also be further diluted with water if desired prior to actual application. In some applications, the activity of these compositions can be enhanced by incorporating into the compositions an adjuvant such as glycerin, methylethylcellulose, hydroxyethylcellulose, polyoxyethylenesorbitan monooleate, polypropylene glycol, polyacrylic acid, polyethylene sodium malate or polyethylene oxide. The adjuvant will generally comprise about 0.1 to about 5% by weight, preferably about 0.5 to about 2% of the composition. Such compositions can also optionally include an agronomically-acceptable surfactant. Typical salts include sodium, potassium, ammonium and amine salts which are water soluble. Long chain amine salts, for example, $C_8$-$C_{18}$ amine can be dissolved in oils and applied as emulsifiable concentrates or by low-volume techniques including Electrodyn (Registered Trademark).

The compounds of formula (I) can be applied as sprays by methods commonly used, such as conventional hydraulic sprays, aerial sprays, and dusts. For ultra-low or low-volume applications a solution of the compound is usually used. The dilution and volume of application will usually depend upon such factors as the type of equipment employed, the method of application, the area to be treated and the type and stage of development of the crop being treated. Oil solutions, suspensions, water-in-oil emulsions, microemulsions and microcapsules can be applied low-volume and undiluted through spinning disc atomisers, or by the electrodynamic spray system.

The following examples illustrate the chemical hybridisation activity of the compounds of formula (I) on dicotyledonous species.

EXAMPLE 1

The object of this test is to determine the efficacy of compounds 1, 2 and 3 of Table I as male sterilants on sunflower, a dicotyledonous species.

Methodology

Sunflower hybrid S-316 was planted in 2 single rows 76 cm apart and 45.7 meters long. When the plants were 30.5 cm, they were thinned to groups of three, 30.5 cm apart with 70 cm between groups. The compounds were applied with a hand-held backpack sprayer fitted with two 80015E flat fan spray tips 45.7 cm apart, delivering 449 lha$^{-1}$ at 25.4 cm spray height.

The compounds were applied when the flower buds averaged either 1-2 cm (early timing) or 3-4 cm (mid timing) in diameter. At an average of 6-7 cm diameter, the ray flowers had started to unfurl. At this time cheesecloth was draped over the head and fastened around the stem with a twist-tie. Bags were re-adjusted as the heads expanded. In each group, the two outer heads were bagged with the middle head left open for cross-pollination. The normal insect population was utilized for pollination. At maturity, the heads were hand harvested and the seed removed manually.

Sterility was determined by a reduction in 100 seed weight and germination. Unlike wheat, sterile florets develop an achene which is somewhat collapsed in appearance. A seed weight reduction of 40% or more (after correction for the effects of bagging) was considered 100% sterile based on visual inspection of representative samples.

A 50 ml volume weight was also determined for each sample, but was not used to determine sterility.

Germination and seedling injury were determined on vermiculite planted 50 seed samples of selected treatments for both bagged and unbagged heads.

The results are presented in Table II.

Discussion

Compound 1 induced male sterility at approximately 4.48 kg ha$^{-1}$ when applied to plants with a 1-2 cm flower bud (the early application stage) and 1.12-2.24 kg ha$^{-1}$ with a 3-4 cm flower bud (the late application stage). Compounds 2 and 3 were applied at 8.96 and 4.48 kg ha$^{-1}$ respectively at the late application stage and both induced a high degree of male sterility at these application rates.

TABLE I

| Compound No | $R^1$ | Salt | $R^2$ | $R^3$ | $R^4$ |
|---|---|---|---|---|---|
| 1 | COO$^-$ | K | 4-chlorophenyl | CH$_3$ | H |
| 2 | COO$^-$ | K | phenyl | CH$_3$ | Br |
| 3 | COO$^-$ | K | phenyl | CH$_3$ | C$_3$H$_7$ |

TABLE II

| Rate kg ha$^{-1}$ | Compound No | (1) | (2) | (3) |
|---|---|---|---|---|
| Early Timing | | | | |
| 0.28 | 1 | 0 | EXCELLENT | EXCELLENT |
| 0.56 | 1 | 0 | EXCELLENT | EXCELLENT |
| 1.12 | 1 | 0 | EXCELLENT | EXCELLENT |
| 2.24 | 1 | 65 | EXCELLENT | EXCELLENT |
| 4.48 | 1 | 95 | EXCELLENT | EXCELLENT |
| 8.96 | 1 | 95 | EXCELLENT | EXCELLENT |
| Mid Timing | | | | |
| 0.28 | 1 | 0 | EXCELLENT | EXCELLENT |
|  | 2 | 0 | FAIR | — |
| 0.56 | 1 | 0 | EXCELLENT | EXCELLENT |
|  | 2 | 0 | FAIR | — |
| 1.12 | 1 | 75 | EXCELLENT | EXCELLENT |
|  | 2 | — | — | — |
| 2.24 | 1 | 95 | EXCELLENT | EXCELLENT |
|  | 2 | 0 | FAIR | — |
| 4.48 | 1 | 95 | EXCELLENT | EXCELLENT |
|  | 2 | 0 | FAIR | EXCELLENT |
|  | 3 | 99 | POOR | POOR |
| 8.96 | 1 | 99 | EXCELLENT | EXCELLENT |

TABLE II-continued

| Rate kg ha$^{-1}$ | Compound No | (1) | (2) | (3) |
|---|---|---|---|---|
| | 2 | 99 | FAIR | EXCELLENT |

Key
(1) Bagged Seed Sterility (determined from 100 seed weight reduction).
(2) Unbagged Head Seed Quality (determined from test weight).
(3) Unbagged Head Seed Set (determined from germination test).

EXAMPLE 2

The object of this experiment was to investigate the effect of timing and dosage of chemical hybridising agent on greenhouse grown safflowers.

Methodology

Safflower S541 (Seedtec International) was grown with three plants per 15.2 cm pots in the greenhouse. Compound no. 1 of Table 1 was applied using normal spray techniques at the following developmental stages—
A) At stage A the plants have an average of 19 leaves which are greater than 2.5 cm long, the central floret is approximately 1 cm in diameter, the two lateral branches are emerged from the upper most nodes with evidence of small branch buds in lower nodes, the leaves are soft and pliable.
B) At stage B the plants have an average of 22-24 leaves which are greater than 2.5 cm long, the central floret is approximately 1 cm in diameter, three lateral branches are emerged from the uppermost nodes and each is 5 cm long, there is evidence of branch buds in lower nodes and the plants are becoming stiffer.
C) At stage C the plants have an average of 26-28 leaves which are greater than 2.5 cm long, the central floret is approximately 1.25 cm in diameter, the lateral branches are developing flower buds and the plants are stiff.
D) At stage D the plants have an average of 28 leaves which are greater than 2.5 cm long, the central floret is approximately 1.5 cm in diameter and the lateral floret buds are approximately 0.5 cm diameter.

The four application times spanned 18 days. The average number of seeds per floret was assessed for both the primary branch and all the other secondary branches. 0.5% Neodol 25-12 was added to the chemical treatments. The results are presented in Table 2. The result for the secondary branches is presented as a single figure overall.

Discussion

Compound no 1 of Table 1 induced male sterility in greenhouse grown safflower over a range of doses and stages. Secondary florets required more chemical hybridising agent than primary florets, but could be sterilised.

TABLE III

| | | Primary Branch | | Secondary Branches | |
|---|---|---|---|---|---|
| Stage | Rate kg/ha | Av Seeds/ Floret | % Seed Reduction | Av Seeds/ Floret | % Seed Reduction |
| A | 0.07 | 1.25 | 94.1 | 7.2 | 28.0 |
| | 0.14 | 1.25 | 94.1 | 6.8 | 32.0 |
| | 0.28 | 0.0 | 100.0 | 0.9 | 91.0 |
| | 0.56 | 0.0 | 100.0 | 0.9 | 91.0 |
| | 1.12 | 0.0 | 100.0 | 0.0 | 100.0 |
| | 2.24 | 0.0 | 100.0 | 0.0 | 100.0 |
| B | 0.07 | 4.5 | 78.9 | 5.5 | 45.0 |
| | 0.14 | 2.0 | 90.6 | 3.3 | 67.0 |
| | 0.28 | 3.0 | 85.9 | 6.1 | 39.0 |
| | 0.56 | 0.0 | 100.0 | 3.0 | 70.0 |
| | 1.12 | 0.0 | 100.0 | 0.0 | 100.0 |
| | 2.24 | 0.0 | 100.0 | 0.0 | 100.0 |
| C | 0.07 | 4.0 | 81.2 | 5.5 | 45.0 |
| | 0.14 | 6.8 | 68.1 | 7.0 | 30.0 |
| | 0.28 | 3.5 | 83.6 | 3.0 | 70.0 |
| | 0.56 | 5.0 | 76.5 | 2.7 | 73.0 |
| | 1.12 | 5.8 | 72.8 | 3.3 | 67.0 |
| | 2.24 | 0.0 | 100.0 | 0.6 | 94.0 |
| D | 0.07 | 7.0 | 67.1 | 5.8 | 42.0 |
| | 0.14 | 4.3 | 79.8 | 7.8 | 22.0 |
| | 0.28 | 1.0 | 95.3 | 3.9 | 61.0 |
| | 0.56 | 2.8 | 86.9 | 3.0 | 70.0 |
| | 1.12 | 3.8 | 82.2 | 4.8 | 52.0 |
| | 2.24 | 5.8 | 72.8 | 6.7 | 33.0 |
| X | 0.0 | 21.3 | — | 10.0 | — |

Key
Av = Average
X = Control

EXAMPLE 3

The object of this experiment was to investigate the effect of timing and dosage of chemical hybridising agent, Compound No 1 of Table 1, on greenhouse grown soya.

Methodology

Seedlings of soya, cv Evans were potted up from modular trays into 12.7 cm pots of low organic matter compost.

The chemical was formulated in 0.5% Triton Ag 98 and 2% glycerol and was applied to the plants using a tracksprayer fitted with a 8004E T-jet nozzle. There were two application rates, 4 and 8 kg/ha and there were two application timings V4 and V7 (Fehr Scale). A fifth treatment involved a split timing with 4 kg/ha applied at each timing. At the first timing (V4) the plants' development was significantly pre-meiosis with either none or very few undeveloped flower buds present. At the second timing (V7) the plants' development was just pre-meiosis or with a few nodes at meiosis. A more detailed explanation of the growth stages can be found in Crop Science, Volume 2, pages 929-931 (Fehr Scale).

There were 5 replicates for each treatment. The plants were given nutrient feeds and treated for pests and diseases regularly. Pod set was assessed at maturity.

Discussion

Compound No 1 of Table 1 considerably reduced the number of fertile pods set over the whole soya plant. There were also a high number of small sterile pods. The compound was highly effective at both rates of application and at the split timing. Female fertility could not be assessed because soya is self-pollinating and no cross-pollinating techniques were used in this test.

TABLE IV

| Timing | Rate (kg/ha) | Number of fertile pods | Number of sterile pods |
|---|---|---|---|
| V4 | 4 | 6.4 | 15.6 |
| V4 | 8 | 0.0 | 50.8 |
| V4 + V7 | 4 + 4 | 0.0 | 47.2 |
| V7 | 4 | 11.6 | 20.2 |

TABLE IV-continued

| Timing | Rate (kg/ha) | Number of fertile pods | Number of sterile pods |
|---|---|---|---|
| V7 | 8 | 0.0 | 48.2 |
| V4 | FB | 23.2 | 2.4 |
| V7 | FB | 20.0 | 3.2 |
|  | UT | 24.4 | 0.6 |

KEY:
FB = Formulation Blank
UT = Untreated Control

EXAMPLE 4

The experiment of Example 3 was repeated in order to confirm the results. The methodology was the same except that only the higher rates were tested. The results are presented in Table V.

TABLE V

| Timing | Rate (kg/ha) | Number of fertile pods | Number of sterile pods |
|---|---|---|---|
| V4 | 8 | 10.2 | 54.6 |
| V4 + V7 | 4 + 4 | 0.0 | 80.8 |
| V7 | 8 | 0.8 | 47.0 |
| V4 | FB | 28.4 | 2.6 |
| V7 | FB | 18.4 | 6.6 |
|  | UT | 26.8 | 4.2 |
|  | UT | 30.2 | 1.6 |

KEY:
FB = Formulation Blank
UT = Untreated Control

EXAMPLE 5

The subject of this experiment was to investigate the effect of timing and dosage of chemical hybridising agent on field-grown sunflowers.

Methodology

This investigation was conducted on two sunflower hybrids, Video and Viky, planted in 2 single rows plots. The experimental design was a randomised block. Compound no. 1 of Table 1 was applied at 3 growth stage timings. At the third stage the plants were tall enough to require the chemical to be applied with a hand held sprayer delivering the same spray volume as the motorised experimental sprayer (500 l/ha). The split application timings were only investigated on hybrid Video.

The application stages were:
1. 6 pairs of leaves.
2. Flower bud being 1.3 cm long.
3. Flower bud being 2.5 cm long.

To assess male sterility, paper bags were placed over between 5 and 8 heads per plot to prevent insect cross-pollination.

At maturity, the bagged heads and a comparable sample of unbagged heads from each plot were hand-harvested, and the seed removed manually.

Male sterility was determined by the reduction in seed set on bagged heads, after correction for the effects of bagging.

The results are presented in Table VI.

TABLE VI

| Application Stage | Rate (kg/ha) | % Sterility (Viky) | % Sterility (Video) |
|---|---|---|---|
| 1 | 1 | — | — |
|  | 2 | — | — |
|  | 4 | 0 | — |
|  | 8 | 0 | 60 |
| 2 | 1 | — | 40 |
|  | 2 | 80 | 75 |
|  | 4 | 97.3 | 96.1 |
|  | 8 | 99.9 | 99.6 |
| 3 | 1 | 75 | 87 |
|  | 2 | 99.2 | 99.0 |
|  | 4 | 100 | 99.9 |
|  | 8 | 99.9 | 100 |
| 1 + 2 | 2 + 1 | — | 83.0 |
|  | 2 + 2 | — | 98.3 |
| 1 + 3 | 2 + 1 | — | 94.4 |
|  | 2 + 2 | — | 100 |
| 2 + 3 | 1 + 1 | — | 99.2 |
|  | 1 + 2 | — | 97.6 |
|  | 2 + 1 | — | 99.8 |
|  | 2 + 2 | — | 100 |

Discussion

The results show that on both hybrids the chemical hybridising agent induced male sterility at approximately 4 kg/ha when applied to plants with a 1-2 cm flower bud and 2 kg/ha with a 2.5-3.5 cm flower bud.

EXAMPLE 7

The experiment presented in this example shows the effect of chemical hybridising agent on Oilseed Rape.

Methodology

Compound no 1 of Table 1 was applied to field grown oilseed rape plants at various rates and at a number of different developmental stages.

The application timings were:
1.0—Plant Height 5 cm
1.5—Plant Height 11 cm
2.0—Plant Height 22 cm
2.5—Plant Height 27 cm
3.0—Plant Height 33 cm The assessment took place at maturity and involved counting the number of pods withmore than one seed per pod on the main infloresence. The heads of the plants were bagged before cross-pollination could occur.

The results are presented in Table VIII.

TABLE VIII

| Application Stage | Rate (kg/ha) | Average Number of pods |
|---|---|---|
| CONTROL | 0 | 30 |
| 1 | 10 | 5 |
| 1.5 | 10 | 15 |
| 2.0 | 8 | 3 |
| 2.0 | 10 | 8 |
| 2.5 | 8 | 20 |
| 2.5 | 10 | 12 |
| 3.0 | 10 | 7 |
| 1.0 + 2.0 | 4 + 4 | 1 |

Discussion

The results show clearly that the chemical hybridising agent has induced male sterility in oilseed rape. In unbagged open pollinated plants, the CHA treated plants gave adequate seed set (female fertility) for hybrid production (50-70%). The level of seed set is sufficient for the initial stages of hybrid seed production.

We claim:
1. A method for inducing male sterility in a dicotyledonous plant selected from the group consisting of sun- flower and safflower which comprises treating the plant with an amount, which is effective to produce male sterility in the plant, of a compound of the formula

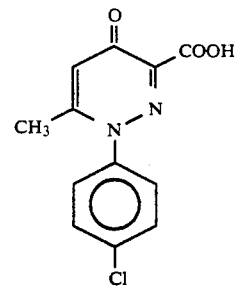

or an agronomically acceptable salt thereof.

2. The method of claim 1 in which the dicotyledonous plant is sunflower.

3. The method of claim 1 in which the dicotyledonous plant is safflower.

4. The method of claim 2 in which the plant is treated with the compound at a rate of 2.24 to 8.96 kg/ha.

5. The method of claim 3 in which the plant is treated with compound at a rate of 0.28 to 2.24 kg/ha.

* * * * *